(12) United States Patent
Gosselin et al.

(10) Patent No.: US 10,752,936 B2
(45) Date of Patent: Aug. 25, 2020

(54) DEVICE FOR ANALYZING A BIOLOGICAL SAMPLE

(71) Applicant: Commissariat a l'energie atomique et aux energies alternatives, Paris (FR)

(72) Inventors: David Gosselin, Grenoble (FR); Jean Berthier, Meylan (FR); Anne-Gaelle Bourdat, Nantoin (FR); Jerome Ventosa, Grenoble (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 566 days.

(21) Appl. No.: 15/464,784

(22) Filed: Mar. 21, 2017

(65) Prior Publication Data
US 2017/0268041 A1 Sep. 21, 2017

(30) Foreign Application Priority Data

Mar. 21, 2016 (FR) ...................................... 16 52378

(51) Int. Cl.
*C12Q 1/6806* (2018.01)
*C12N 1/06* (2006.01)
(Continued)

(52) U.S. Cl.
CPC .......... *C12Q 1/6806* (2013.01); *C12N 1/066* (2013.01); *C12N 15/1017* (2013.01);
(Continued)

(58) Field of Classification Search
CPC ...... C12Q 1/6806; C12Q 1/686; G01N 1/286; G01N 2001/2866; C12N 1/066; C12N 15/1017
See application file for complete search history.

(56) References Cited

U.S. PATENT DOCUMENTS 3,941,317 A * 3/1976 Kanor .................... C12M 45/02
241/21
5,114,858 A * 5/1992 Williams ............... C12M 47/06
422/527
(Continued)

FOREIGN PATENT DOCUMENTS

WO WO 99/28742 6/1999
WO WO 2015/181743 A1 12/2015

OTHER PUBLICATIONS

French Preliminary Search Report dated Jan. 6, 2017 in French Application 16 52378 filed on Mar. 21, 2016 (with English Translation of Categories of Cited Documents).

*Primary Examiner* — Sally A Merkling
(74) *Attorney, Agent, or Firm* — Oblon, McClelland, Maier & Neustadt, L.L.P.

(57) ABSTRACT

A device for analyzing a biological sample which includes a separation and detection chamber into which an injection channel and a discharge channel open, a filter separating the chamber into two distinct spaces so as to define a first space into which the injection channel opens and a second space into which the discharge channel opens, the filter having a porosity suitable for the separation to be carried out, a rough bearing surface having a surface roughness parameter suitable for carrying out a mechanical lysis of the biological species present in the sample, the bearing surface being arranged in the first space, a flexible membrane arranged opposite the rough bearing surface relative to the filter and blocking an opening made through the housing.

12 Claims, 2 Drawing Sheets

(51) Int. Cl.
    *G01N 1/28*         (2006.01)
    *C12N 15/10*      (2006.01)
    *C12Q 1/686*      (2018.01)

(52) U.S. Cl.
    CPC .............. *C12Q 1/686* (2013.01); *G01N 1/286* (2013.01); *G01N 2001/2866* (2013.01)

(56) References Cited

U.S. PATENT DOCUMENTS

2003/0066915 A1    4/2003  Taylor
2016/0069916 A1*  3/2016  Loo ......................... G01N 1/38
                                                                 435/34

* cited by examiner

DEVICE FOR ANALYZING A BIOLOGICAL SAMPLE

TECHNICAL FIELD OF THE INVENTION

The present invention relates to a device for analyzing a biological sample comprising biological species. This analyzing device makes it possible in particular to carry out a concentration and purification of biological species present in the sample, a lysis of these biological species with a view to extracting therefrom the biological material to be analyzed, then a separation of this biological material and an amplification reaction with a view to detection of a pathogen in the sample.

PRIOR ART

The detection of pathogens in a biological sample is often carried out by using a bulky material that is not very suitable, in particular for rapid analysis in the field. The detection requires in particular a step of lysis of the biological species contained in the sample in order to grind said species, after concentration and purification steps.

Devices which make it possible to carry out the concentration, purification and mechanical lysis steps are known in the prior art. Patent application WO 20151181743A1 describes in particular such a device. In said device, the mechanical lysis is carried out by shearing between two walls, one of the two walls having a rough bearing surface. Such a device essentially makes it possible to carry out the grinding and is not suitable for performing a more complete analysis of a biological sample.

There are moreover solutions which make it possible to carry out a detection of the presence of pathogen by amplification and detection by colorimetry or turbidity or pH measurement. Such solutions are for example described in the following publications:

"*Visual detection of isothermal nucleic acid amplification using pH-sensitive dyes*", Nathan A. Tanner et al.—BioTechniques, Vol. 58, n° 2, February 2015, pp. 59-68.

"*Colorimetric detection of loop-mediated isothermal amplification reaction by using hydroxy naphthol blue*", Motoki Goto et al.—BioTechniques, Vol. 46, No. 3, March 2009, pp. 167-172.

"*Loop-Mediated Isothermal Amplification Assay for Rapid Detection of Common Strains of Escherichia coli*", Hill J, Beriwal S, Chandra I, et al.—Journal of Clinical Microbiology. 2008; 46(8):2800-2804. doi:10.1128/JCM.00152-08.

"*Visual Detection of Norovirus Genogroup II by Reverse Transcription Loop-Mediated Isothermal Amplification with Hydroxynaphthol Blue Dye*", Jianming, Ziqian Xu, Kai Nie, Xiong Ding, Li Guan, Ji Wang, Yuying Xian, Xiyang Wu, Xuejun Ma—Food and Environmental Virology, September 2014, Volume 6, Issue 3, pp. 196-201.

However, there is no device which makes it possible to carry out an overall and complete analysis of a biological sample and which is:
Easily transportable,
Simple to use,
Reliable,
Inexpensive.

The aim of the invention is to provide a device for analyzing a biological sample which makes it possible to achieve these various objectives.

SUMMARY OF THE INVENTION

This aim is achieved by means of a device for analyzing a biological sample comprising biological species, said device comprising:
A housing comprising at least one opening,
An injection channel made in said housing and via which said biological sample can be injected in the form of a fluid,
A discharge channel made in said housing,
A chamber into which the injection channel and the discharge channel open,
A filter separating said chamber into two distinct spaces, so as to define a first space into which said injection channel opens and a second space into which said discharge channel opens, said filter having a porosity suitable for the separation to be carried out,
A rough bearing surface having a surface roughness parameter suitable for carrying out a mechanical lysis of said biological species, said bearing surface being arranged in said first space, said filter comprising at least one part having an elastic deformability sufficient to reach said rough bearing surface during the exertion of a bearing force,
A flexible membrane arranged opposite the rough bearing surface relative to the filter and blocking the opening made through the housing.

With respect to the prior art, it is in particular understood that the architecture of the device makes it possible to clearly dissociate the functions of separation and of mechanical lysis. This has in particular the advantage of being able to perform one of the two steps, without necessarily performing the other. In addition, this also makes it possible to modify the characteristics of the filter independently of the characteristics of the rough bearing surface for carrying out the lysis.

In addition, the architecture of the device will advantageously make it possible to carry out the separation in the chamber, while maintaining in the chamber both the pollutants (in the first space of the chamber) and the biological material to be studied (in the second space of the chamber).

According to one particularity, the membrane is made of a transparent material. This will in particular make it possible to carry out a detection by visualizing the content of the chamber through the membrane.

According to another particularity, the housing comprises at least one wall made of a transparent material.

According to another particularity, the device comprises heating means arranged so as to heat the chamber to a given temperature.

According to another particularity, the housing comprises a lower wall, a side wall and an upper wall.

According to another particularity, the injection channel and the discharge channel are for example made through said upper wall of the housing.

According to another particularity, said opening blocked by the membrane is for example made through the upper wall of the housing.

According to another particularity, the rough bearing surface has a mean surface roughness parameter of for example between 0.1 µm and 10 µm.

According to another particularity, the filter has pores which have a mean diameter of for example between 0.2 µm and 0.5 µm.

The invention also relates to a method for analyzing a biological sample, carried out by means of the device as described above, this method thus comprising at least the following steps:

Injection of a sample containing biological species into the first space of the chamber of the device via the injection channel, Mechanical lysis of the biological species present in the chamber by grinding against the rough bearing surface in order to release a biological material to be analyzed, Separation of the biological material with respect to the pollutants by filtering through the filter while passing the biological material into the second space of the chamber and while maintaining pollutants in the first space, Amplification of the biological material by heating the chamber to a given temperature, Analysis of the biological material obtained after amplification.

According to one particularity, the method may also comprise a step of rinsing and of purification of the biological species present in the chamber, carried out before the mechanical lysis step.

According to another particularity, the analysis step is for example carried out by colorimetry, electrochemical measurement, turbidity measurement or fluorescence.

BRIEF DESCRIPTION OF THE FIGURES

Other characteristics and advantages will become apparent in the detailed description which follows, given with regard to the appended drawings in which.

DETAILED DESCRIPTION OF AT LEAST ONE EMBODIMENT

Figure 1A:
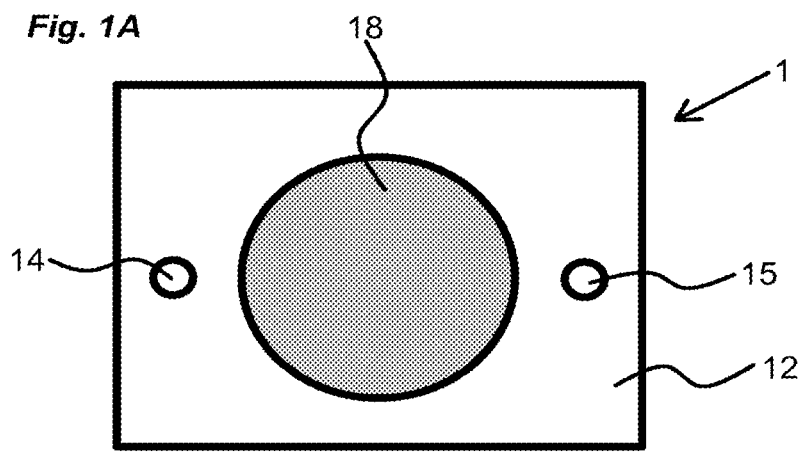
FIGS. 1A and 1B represent, diagrammatically, respectively viewed from below and viewed from the side, the device for analyzing a biological sample according to the invention.
Figure 1B:
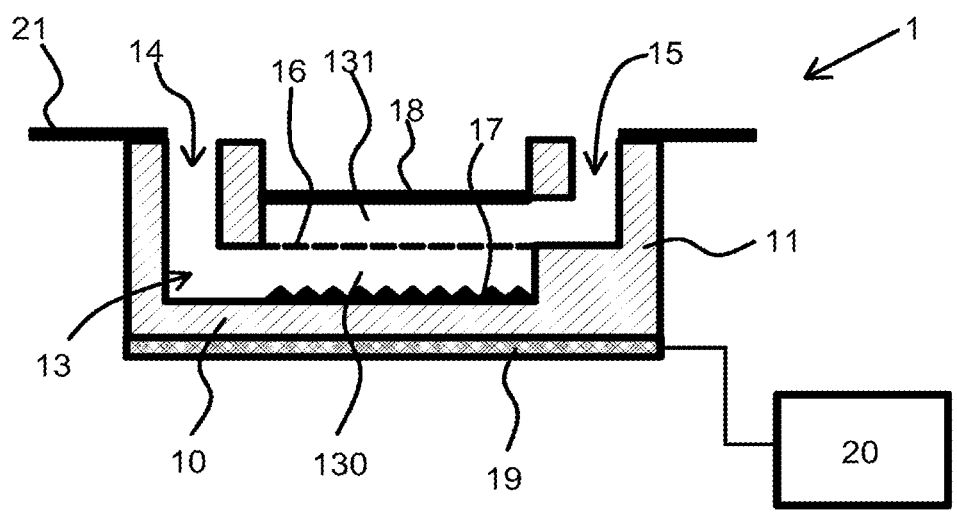

The device of the invention is intended for the analysis of a biological sample. This biological sample is for example in the form of a fluid which contains biological species containing a biological material to be studied. The term "biological species" is intended to mean in particular microorganisms, cells, spores, etc. The term "biological material to be studied" is intended to mean for example nucleic acid (RNA, DNA) molecules from a cell, proteins, lipopolysaccharides (LPSs), lipoteichoic acids (LTAs), etc.

The term "fluid" is intended to mean in particular a liquid, a gas, etc. The liquid may exhibit various degrees of viscosity and may for example be in the form of a paste or of a gel.

Advantageously, the invention has the particularity of being able to carry out, in one and the same device, equally:

A purification and a concentration of the biological species present in the biological sample, A mechanical lysis of the biological species present in the sample with a view to extracting therefrom a biological material to be studied, A separation between the biological material to be studied and pollutants that are present, and A detection of pathogen presence in the biological material which has been separated.

In the remainder of the description, the terms "lower", "upper", "top" and "bottom" used should be understood by taking as reference a principal axis which is vertical.

In the remainder of the description, the terms "external", "exterior", "internal" and "interior" should be understood by taking as reference the chamber of the device, which will be described below.

The device 1 comprises a housing. The housing comprises a lower wall 10, a side wall 11 and an upper wall 12. All the walls of the housing will preferentially be made of one and the same material. This material will in particular be suitable for being able to undergo heating in a temperature range of between 20° C. and 100° C. Preferentially, some walls of the housing, at least its side wall 11, will be made of a transparent material. Preferentially, the material used will be a plastic, for example of PMMA (poly(methyl methacrylate)) type.

The device 1 comprises a chamber 13 made in the housing. This chamber represents the place in which are carried out equally the purification/concentration, the mechanical lysis, the separation and optionally the detection in the biological species. The chamber 13 is closed toward the bottom by the lower wall of the housing.

The device comprises an injection channel 14 for injecting therein all types of fluids, for example by means of a pipette. The injection channel comprises an inlet made, for example, through the upper wall 12 of the housing and an outlet which opens into said chamber 13. The inlet of the injection channel 14 is, for example, arranged vertically and its outlet opens for example horizontally into the chamber 13. The inlet of the injection channel is for example widened out in order to apply thereto the tip of a pipette or will be adapted to the type of device used to inject the fluid into the device. By way of example, it will be an inlet which has a joining piece of luer type for connecting a syringe thereto.

The device comprises a discharge channel 15, the inlet of which communicates with the space formed by the chamber 13 and the outlet of which communicates with the exterior via an opening made for example through the upper wall of the housing. Injected fluids are discharged via this discharge channel 15. Its inlet is for example arranged horizontally and its outlet vertically. The chamber 13 is placed between the injection channel 14 and the discharge channel 15.

Toward the top, the chamber 13 is closed by a flexible and stretchable, preferentially transparent, membrane 18. The upper wall 12 of the housing of the device thus comprises an opening which is hermetically covered by said membrane 18. Said membrane is thus anchored in the housing by any suitable attaching solution, for example by adhesive bonding. This membrane 18 will for example be composed of a film, for example of the type MicroAmp, 3M (registered trademarks), having a thickness, dimensions and a make-up suitable for elastically deforming, relative to its anchoring points, in particular to the bottom of the chamber 13.

The term "transparent" is intended to mean that the material used is at least partially transparent to visible light, so as to allow at least 80% of this light to pass through. It should thus be understood that it will be sufficiently transparent to see the interior of the chamber 13, at least the second space located above the filter.

The device comprises a filter 16 arranged in said chamber 13 and separating said chamber 13 into two spaces. The two spaces are for example superimposed and thus denoted lower space 130 located under the filter and upper space 131 located above the filter. This filter 16 is preferentially totally or partly made in the form of a thin flexible film, pulled in the space formed by the chamber so as to allow passage from one space to the other only via the pores of the filter 16. The film exhibits an elastic deformability which allows it to stretch during the exertion of a bearing force in a substantially vertical direction, this elastic deformability having a level sufficient to reach the lower surface of the chamber 13. The filter 16 has a mean pore diameter of between 0.2 μm and 50 μm, for example of between 0.2 μm and 1 μm for the separation of microorganisms. The pore diameter is of course adapted to ensure a separation between the pollutants and the biological material to be studied. After the lysis step and the separation by the filter 16, the biological material to be studied remains above the filter 16, in the upper space 131 of the chamber, while the pollutants remain below the filter, in the lower space 130 of the chamber. The filter 16 will for example be composed of a film having a thickness, dimensions and a make-up suitable for deforming to the bottom of the chamber 13 relative to its anchoring points. According to one particular embodiment, the film may also be made of a transparent material, for example with the same transparency characteristics as the membrane.

The device comprises a rough bearing surface 17 arranged on the bottom of the chamber 13. This rough bearing surface 17 extends over a major part of the bottom of the chamber. It comprises a mean surface roughness parameter of between 0.1 μm and 10 μm, preferentially between 0.2 μm and 3 μm. This rough bearing surface 17 is intended to allow a mechanical lysis of the biological species present in a biological sample placed in the device. Preferentially, the mechanical lysis is carried out by grinding said biological species, by abrasion on said rough bearing surface. The grinding operation is carried out by a friction movement of the biological species against the rough bearing surface, using a suitable grinding member. This member will for example be a spatula 2 (see FIG. 2B) or a rod, for example made of plastic or metal. This member is applied from the exterior of the chamber 13 and its end is applied against the external surface of the membrane 18 so as to stretch the membrane 18 and the filter toward the bottom of the chamber and thus to rub the biological species present in a sample against the rough bearing surface.

The device will preferentially comprise means for blocking the injection channel and the discharge channel in order to close any access to the chamber and to isolate the internal space of the chamber relative to the exterior. These means are for example made of two flaps 21, the position of which makes it possible to block or to open each channel 14, 15 or made of adhesives stuck onto the inlet of the injection channel and the outlet of the discharge channel. Other solutions could of course be envisioned.

Preferentially, the housing can integrate means for heating the internal space of the chamber, composed for example of at least one heating resistor 19, as represented in the appended figures. The resistor is for example attached under the lower wall of the housing. A power source 20 will for example be envisioned for powering the resistor 19. The power source will comprise for example one or more electric batteries, providing sufficient energy to heat the chamber to a temperature included in the range defined above, that is to say from 20° C. to 100° C. Of course, other heating means could be used, comprising for example a conductive ink deposited by printing or screen printing under the lower wall of the housing.

Thus, to summarize, the device comprises the following "multilayer" structure:
A lower rough bearing surface 17,
A lower space 130 of a chamber 13 located above the rough bearing surface 17,
A flexible and stretchable filter 16 located above the lower space 130,
An upper space 131 of the chamber 13 located above the filter 16,
A flexible and stretchable membrane 18 located above the upper space 131, hermetically closing the chamber and accessible from the exterior of the device.

Using the device described above, in a nonlimiting manner, a lysis, separation and detection method will comprise for example the following steps:
The liquid biological sample, comprising biological species 3, is injected into the chamber 13 of the device 1 by means of a pipette, via the injection channel 14. By way of example, the sample has a volume of 1 milliliter and contains $10^5$ bacteria per milliliter. The liquid part of the sample and all the particles/molecules which pass through the filter 16 are recovered via the discharge channel 16 and discarded from the analysis. The bacteria are then concentrated in the lower space 130 of the chamber 13. Pollutants present in the sample, too large to pass through the filter, can also remain in the lower space 130 of the chamber 13.

Figure 2A:
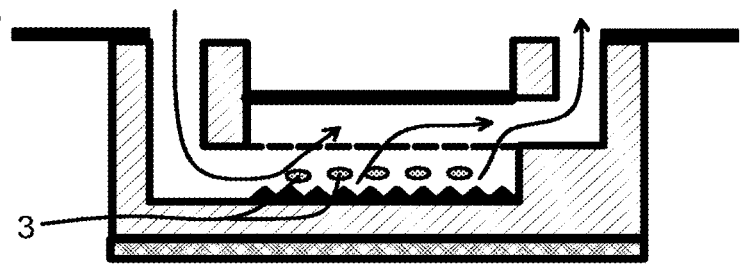
FIGS. 2A to 2E illustrate the various steps of a method of analysis and detection carried out by virtue of the device of the invention.

Once the sample is present in the chamber, a solution for washing/rinsing the biological species 3 present is preferentially injected by means of a pipette via the injection channel 14, so as to purify the bacteria present in the sample (FIG. 2A). Pollutants 31, which are too large to pass through the filter 16 and insoluble, can also remain in the space 130.

Figure 2B:
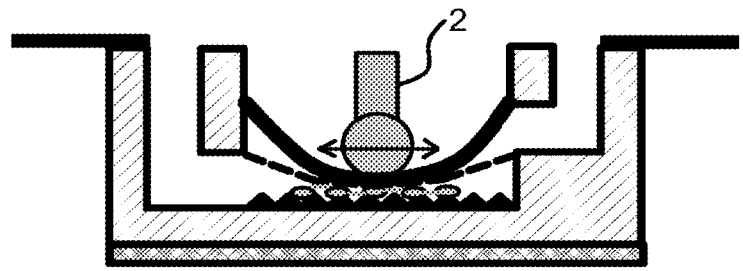

A mechanical lysis of the biological species 3 is carried out by means of a spatula 2. The end of the spatula 2 is brought into contact with the external surface of the membrane 18, then, by pushing on the membrane 18 so as to stretch it toward the interior of the chamber 13, the end of the spatula 2 reaches the rough bearing surface 17 so as to grind the biological species 3 against the rough bearing surface (FIG. 2B).

Figure 2C:
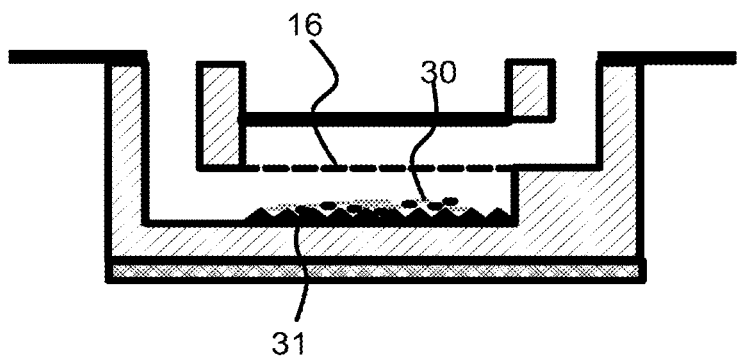

Once the mechanical lysis has been carried out, the lower space of the chamber comprises the biological material 30 to be studied, for example DNA molecules, and pollutants 31 (FIG. 2C).

Figure 2D:
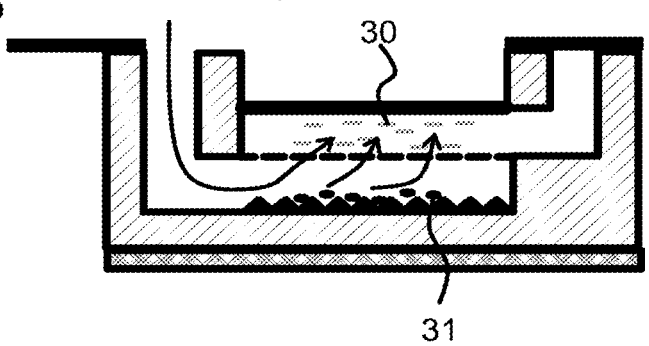

In order to perform the separation between the biological material 30 to be studied and the pollutants 31, a liquid solution containing amplification reagents is injected into the chamber via the injection channel 14, in order to elute the biological material to be studied. A part of the liquid solution injected thus carries away the biological material 30 to be studied, for example the DNA molecules, passes through the filter 16 and returns to the upper space 131 of the chamber. The pollutants 31, which have a structure that is larger in diameter than the pores of the filter 16, remain in the lower space 130 of the chamber 13. During this step, the discharge channel 15 is preferentially blocked by a flap 21 so as to prevent any discharge of the biological material 30 to be studied (FIG. 2D).

Once the separation between the pollutants 31 and the biological material 30 to be studied has been performed, it is a question of carrying out a reaction for amplification of the biological material in order, for example, to be able to detect the presence of a pathogen in the biological material 30 that has been separated.

The amplification reaction is carried out by heating the internal space of the chamber 13, for example by means of the system of resistors 19 integrated into the housing. During the heating operation, the injection channel 14 and the discharge channel 15 are preferentially closed.

Figure 2E:
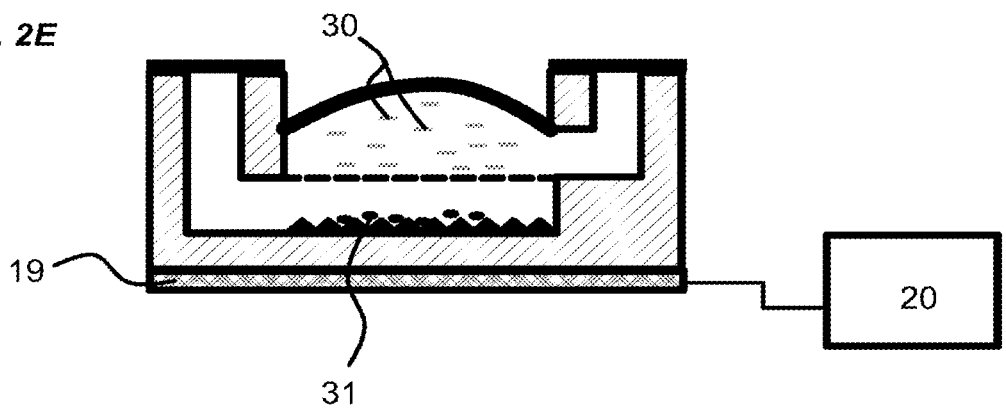

The temperature at which the chamber 13 is heated depends on the type of amplification reaction carried out. It may be any type of amplification reaction, for example LAMP (Loop-Mediated Isothermal Amplification), PCR (Polymerase Chain Reaction), NASBA (Nucleic Acid Sequence Based Amplification), RPA (Recombinase Polymerase Amplification), etc. For an amplification of LAMP type, the heating is carried out at a temperature advantageously of between 60° C. and 65° C. This reaction makes it possible to amplify the molecules of the biological material 30 to be detected, for example the DNA molecules. During the heating, the membrane 18 is for example made to stretch so as to create a concavity in the chamber 13, thus increasing the volume of the chamber (FIG. 2E).

During the reaction for amplification of the biological material, it is a question of detecting whether a pathogen is present. For this, it is possible to use various methods, for instance colorimetry, fluorescence, electrochemistry, pH-metry, turbidity measurement. Any other detection method could be envisioned. For a detection method of pH-metry, pH detection electrodes could be integrated into the device. During a detection by colorimetry or fluorescence, the transparent characteristic of the membrane 18 and/or of the housing of the device, in particular at the level of its side wall, has the advantage of allowing direct visual detection. Thus, by observing the color of the sample present in the chamber, it is possible to determine whether or not a pathogen is present.

The device of the invention thus comprises numerous advantages, among which:

A device that is easily transportable, since it is light and not very bulky.

A device which makes it possible to carry out, in one and the same chamber, equally the concentration/purification, the lysis, the separation, the amplification and the detection, thus forming a Lab-On-Chip.

A device which comprises no complex mechanical part for carrying out the mechanical lysis.

A device which optionally allows detection by colorimetry, just by looking through the transparent parts of the device.

The invention claimed is:

1. A device for analyzing a biological sample comprising biological species, said device comprising:
    a housing comprising an opening,
    an injection channel made in said housing and via which said biological sample can be injected in the form of a fluid,
    a discharge channel made in said housing,
    a rough bearing surface having a surface roughness parameter suitable for carrying out a mechanical lysis of said biological species,
    a chamber into which the injection channel and the discharge channel open, said chamber including a first space and a second space, said first space being located above said rough bearing surface,
    a filter located above said first space, separating said chamber into two distinct spaces so as to define said first space into which said injection channel opens and said second space into which said discharge channel opens, said filter having a porosity suitable for the separation to be carried out, said filter comprising at least one part having an elastic deformability sufficient to reach said rough bearing surface of the chamber during the exertion of a bearing force, said second space being located above said filter, and
    a flexible membrane located above said second space and blocking said opening of the housing.

2. The device as claimed in claim 1, wherein the membrane is made of a transparent material.

3. The device as claimed in claim 1, wherein the housing comprises at least one wall made of a transparent material.

4. The device as claimed in claim 1, further comprising a heating device arranged so as to heat the chamber to a given temperature.

5. The device as claimed in claim 1, wherein the housing comprises a lower wall, a side wall and an upper wall.

6. The device as claimed in claim 5, wherein the injection channel and the discharge channel are made through said upper wall of the housing.

7. The device as claimed in claim 5, wherein said opening blocked by the membrane is made through the upper wall of the housing.

8. The device as claimed in claim 1, wherein the rough bearing surface has a mean surface roughness parameter of between 0.1 µm and 10 µm.

9. The device as claimed in claim 1, wherein the filter has pores which have a mean diameter of between 0.2 µm and 0.5 µm.

10. A method for analyzing a biological sample using the device as claimed in claim 1, the method comprising:
    injecting a sample containing biological species into the first space of the chamber of the device by the injection channel,
    mechanical lysis of the biological species present in the chamber by grinding against the rough bearing surface in order to release a biological material to be analyzed,
    separating the biological material with respect to the pollutants by filtering through the filter while passing the biological material into the second space of the chamber and while maintaining pollutants in the first space,
    amplifying the biological material by heating the chamber to a given temperature, and
    analyzing the biological material obtained after amplification.

11. The method as claimed in claim 10, further comprising rinsing and purifying the biological species present in the chamber, carried out prior to the mechanical lysis step.

12. The method as claimed in claim 10, wherein the analyzing is carried out by colorimetry, electrochemical measurement, turbidity measurement or fluorescence.

* * * * *